United States Patent
Earl et al.

(10) Patent No.: US 8,795,282 B2
(45) Date of Patent: Aug. 5, 2014

(54) APPARATUS AND METHOD FOR THE EXTRAMEDULLARY LOCATION OF THE MECHANICAL AXIS OF A FEMUR

(75) Inventors: Brian D. Earl, South Bend, IN (US); Anthony P. Romano, Columbia City, IN (US); Jody L. Claypool, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 771 days.

(21) Appl. No.: 12/695,804

(22) Filed: Jan. 28, 2010

(65) Prior Publication Data

US 2010/0191298 A1      Jul. 29, 2010

Related U.S. Application Data

(60) Provisional application No. 61/148,255, filed on Jan. 29, 2009.

(51) Int. Cl.
| | |
|---|---|
| *A61B 17/56* | (2006.01) |
| *A61B 17/15* | (2006.01) |
| *A61F 2/46* | (2006.01) |
| *A61F 2/30* | (2006.01) |

(52) U.S. Cl.
CPC ......... *A61F 2/4657* (2013.01); *A61F 2002/469* (2013.01); *A61B 17/155* (2013.01); *A61F 2220/0025* (2013.01); *A61F 2002/4658* (2013.01); *A61F 2002/3052* (2013.01); *A61F 2002/4668* (2013.01)
USPC ........................................................ 606/86 R

(58) Field of Classification Search
CPC .................. A61B 17/56; A61B 17/155; A61B 2002/3052; A61B 2002/4668; A61B 2/4657
USPC ..................................... 606/86 R, 87–89, 102
See application file for complete search history.

(56) References Cited

U.S. PATENT DOCUMENTS

| | | | | |
|---|---|---|---|---|
| 4,989,337 A | * | 2/1991 | Mason et al. | ............ 33/512 |
| 5,478,341 A | * | 12/1995 | Cook et al. | ............ 606/62 |

(Continued)

FOREIGN PATENT DOCUMENTS

| | | |
|---|---|---|
| DE | 102007024708 A1 | 11/2008 |
| FR | 2885293 A1 | 11/2006 |
| KR | 2003-0033119 A | 5/2003 |

OTHER PUBLICATIONS

The International Preliminary Report on Patentability mailed Aug. 11, 2011 in the related International Application No. PCT/US2010/022400.

(Continued)

*Primary Examiner* — Christopher Beccia
(74) *Attorney, Agent, or Firm* — Schwegman Lundberg & Woessner, P.A.

(57) ABSTRACT

A surgical instrument and method determine the orientation of the mechanical axis of a femur. The instrument may include a rod with a first end of the rod rotatably secured at a first point on the surface of distal femur that corresponds to center of the knee joint so that the first end is coincident with the mechanical axis. The connection between the first end of the rod and the distal end of the femur defines a first point of rotation. The second end of the rod is slideably received within a sleeve that is rotatably connected to a support positioned distally away from the distal end of the femur. The connection between the sleeve and the support defines a second point of rotation. When the distance between the first and second points of rotation is minimized, a line drawn therebetween is coincident with the mechanical axis of the femur.

12 Claims, 4 Drawing Sheets

(56) References Cited

U.S. PATENT DOCUMENTS

| | | | |
|---|---|---|---|
| 5,520,694 | A | 5/1996 | Dance et al. |
| 5,690,638 | A * | 11/1997 | Dance et al. .................... 606/88 |
| 6,299,616 | B1 * | 10/2001 | Beger .......................... 606/86 R |
| 7,011,664 | B2 * | 3/2006 | Haney et al. .................... 606/87 |
| 7,134,216 | B2 * | 11/2006 | Rupp et al. ...................... 33/512 |
| 7,892,240 | B2 * | 2/2011 | Claypool et al. .............. 606/102 |
| 2007/0162038 | A1 * | 7/2007 | Tuke ............................... 606/88 |
| 2008/0051798 | A1 * | 2/2008 | Colquhoun et al. ............ 606/87 |
| 2008/0208203 | A1 * | 8/2008 | Moindreau et al. ........... 606/102 |
| 2009/0216247 | A1 * | 8/2009 | Collette ......................... 606/130 |
| 2009/0222010 | A1 * | 9/2009 | Lafosse et al. .................. 606/87 |
| 2009/0270875 | A1 * | 10/2009 | Poncet .......................... 606/102 |
| 2010/0131021 | A1 * | 5/2010 | Rock et al. .................. 606/86 R |

OTHER PUBLICATIONS

The International Search Report and Written Opinion mailed May 4, 2010, of International Application No. PCT/US2010/022400.

* cited by examiner

FIG_5

FIG_6

FIG_7

APPARATUS AND METHOD FOR THE EXTRAMEDULLARY LOCATION OF THE MECHANICAL AXIS OF A FEMUR

CROSS REFERENCE TO RELATED APPLICATION

This application claims the benefit under Title 35, U.S.C. §119(e) of U.S. Provisional Patent Application Ser. No. 61/148,255, entitled APPARATUS AND METHOD FOR THE EXTRAMEDULLARY LOCATION OF THE MECHANICAL AXIS OF A FEMUR, filed on Jan. 29, 2009, the entire disclosure of which is hereby expressly incorporated herein by reference.

BACKGROUND

1. Field of the Invention

The present invention relates to a surgical instrument and methods for using the same.

2. Description of the Related Art

In order to prepare the distal end of a femur for receipt of an orthopedic component, such as in a total knee arthroplasty, it may be necessary to determine the location of the mechanical axis of the femur. The human femur is generally referred to as having two discrete axes, an anatomical axis and a mechanical axis. The anatomical axis of the femur extends along the longitudinal axis of the shaft of the femur. The mechanical axis of the femur extends from the center of the head of the femur to the center of the knee joint and is the weight bearing axis of the femur. Thus, when an orthopedic component is being implanted on the distal end of the femur, it may be necessary to identify the mechanical axis, i.e., the weight bearing axis, of the femur in order to properly align the orthopedic component within the knee joint.

SUMMARY

The present disclosure provides a surgical instrument for the determination of the mechanical axis of the femur and methods for using the same. In one exemplary embodiment, the instrument includes a rod having opposing first and second ends. The first end of the rod is rotatably secured at a first point on the surface of the distal femur that corresponds to the center of the knee joint and, thus, is coincident with the mechanical axis. The first end of the rod is rotatably secured to the femur in a manner that provides the rod with three rotational degrees of freedom, while substantially preventing translation of the rod relative to the femur, i.e., provides no translational degree of freedom. In one exemplary embodiment, the rod is secured to the femur using a ball joint. In another exemplary embodiment, the rod may have a sharpened tip or stylus which pierces the cartilage of the knee to couple the tip to the distal end of the femur. In this manner, the connection between the first end of the rod and the distal end of the femur defines a first point of rotation.

The second end of the rod is slideably received within a sleeve that is rotatably connected to a support, which may be positioned at any arbitrary location that is spaced distally away from the distal end of the femur. The sleeve is rotatably secured to the support in a manner that provides the sleeve with three rotational degrees of freedom, while substantially preventing translation of the sleeve relative to the support, i.e., provides no translational degree of freedom. In one exemplary embodiment, the sleeve is secured to the support using a ball joint. The connection between the sleeve and the support defines a second point of rotation.

With the rod secured to the distal femur and slidably received within the sleeve, as indicated above, the femoral head of the femur may be rotated against the acetabulum until a minimum distance between the first point of rotation and the second point of rotation, i.e., between the connection of the first end of the rod and the femur and the connection between the sleeve and the support, is identified. When the minimum distance between the first and second points of rotation is identified, the location of the mechanical axis of the femur is also identified. Specifically, when the femur is positioned such that the minimum distance between the first and second points of rotation is reached, a line drawn between the first and second points of rotation is substantially collinear with the mechanical axis of the femur. With the location of the mechanical axis of the femur determined, the distal end of the femur may be marked and bone preparation instruments may be oriented along the mechanical axis to facilitate the preparation of the femur for the receipt of an orthopedic component.

In one exemplary embodiment, the rod and sleeve may cooperate to form a ratchet mechanism that allows for translation of the rod relative to the sleeve in a single direction. Specifically, the ratchet mechanism allows for the rod to be advanced into the sleeve, but prevents the rod from being advanced out of the sleeve. Thus, in order to identify the minimum distance between the first and second points of rotation, a surgeon may rotate the patient's femur and advance the rod into the sleeve until reaching a point at which any subsequent movement of the patient's femur fails to result in further advancement of the rod into the sleeve. Once this occurs, the rod and sleeve are retained by the ratchet mechanism in a position relative to one another that defines the minimum distance between the first and second points of rotation. In another exemplary embodiment, the rod may have a series of gradations that indicate the distance at which the rod has been advanced into the sleeve. By visually monitoring the gradations on the rod, the surgeon may visually determine the point at which the rod is advanced the furthest into the sleeve. Based in this visual determination, the position at which the minimum distance between the first and second points of rotation is achieved can be identified. In still other exemplary embodiments, the relative distance of the rod tip from the sleeve is measured and monitored for an inflection point at which the distance changes from decreasing to increasing. The position corresponding to the minimum distance between the first and second points of rotation is the position at which this inflection point occurs.

Advantageously, the device and method of the present disclosure overcomes the problems of intramedullary mechanical axis location devices by avoiding the need to violate the intramedullary canal of the femur in order to determine the location of the mechanical axis. Also, an increased strain on the muscles of the patient's leg is avoided, which eliminates the potential for dislocating the femoral head from the acetabulum during use. Further, the device and method of the present disclosure eliminates the need for a surgeon to estimate the position of the femoral head and/or the anatomical axis of the femur and, correspondingly, eliminates the potential for an inaccurate estimate.

In one form thereof, the present invention provides a method of determining the location of a mechanical axis of a femur spanning a knee joint and a hip joint, the method including the steps of: selecting a first point of rotation corresponding with the center of the knee joint; selecting a second point of rotation spaced apart from the first point of rotation, the second point of rotation distal of the femur; and establishing a minimum distance between the first point of rotation and the second point of rotation by rotating the femur about the hip joint. The first point of rotation and the second point of rotation define endpoints of a line segment that is coincident with the mechanical axis of the femur when the minimum distance is established.

In one aspect, the step of selecting a first point of rotation includes rotatably coupling an end of an elongate rod to the distal end of the femur at a position corresponding to the center of the knee joint to define the first point of rotation, with the rod having three rotational degrees of freedom relative to the femur, and with the rod constrained from translation relative to the femur. The step of selecting a second point of rotation includes rotatably coupling an elongate base to a support to define the second point of rotation, with the base having three rotational degrees of freedom relative to the support, and with the base constrained from translation relative to the support. The step of establishing a minimum distance comprises rotating the femur to translate the rod along a longitudinal axis of the base until the minimum distance is established.

In another form thereof, the present invention provides a surgical instrument for determining the mechanical axis of a bone including a support, an elongate base having a pivot end rotatably coupled to the support with three degrees of rotational freedom, an elongate rod having a bone-contacting end adapted to be rotatably coupled to a bone with three rotational degrees of freedom, and an indicator in communication with the base and the rod. The rod is slidably coupled to the base, and the indicator measures a relative position of the rod to the base.

In yet another form thereof, the present invention provides a surgical instrument for determining the mechanical axis of a bone including a means for supporting the surgical instrument, an elongate base having a pivot end rotatably coupled with the support means, an elongate rod, and a measurement means operatively coupled to the rod and the body. The elongate base has three degrees of rotational freedom relative to the bone, and the elongate base is constrained from translation relative to the femur. The elongate rod has a bone-contacting end adapted to be rotatably coupled to a bone with three rotational degrees of freedom relative to the bone, and the rod is constrained from translation relative to the femur. The rod is slidably coupled to the base, and the measurement means are for measuring a distance between the bone-contacting end of the rod and a point on the base.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

Figure 1:
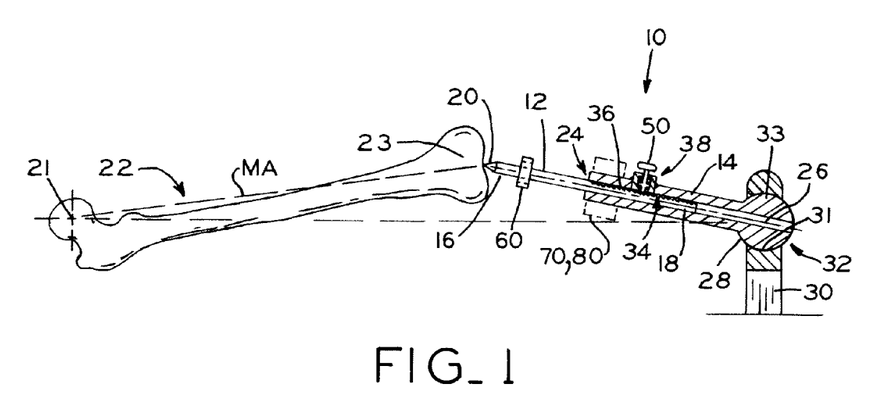
FIG. 1 is a partial cross-sectional view of the surgical instrument in accordance with the present disclosure depicting the surgical instrument connected to the distal end of a femur with a stylus.
Figure 2:
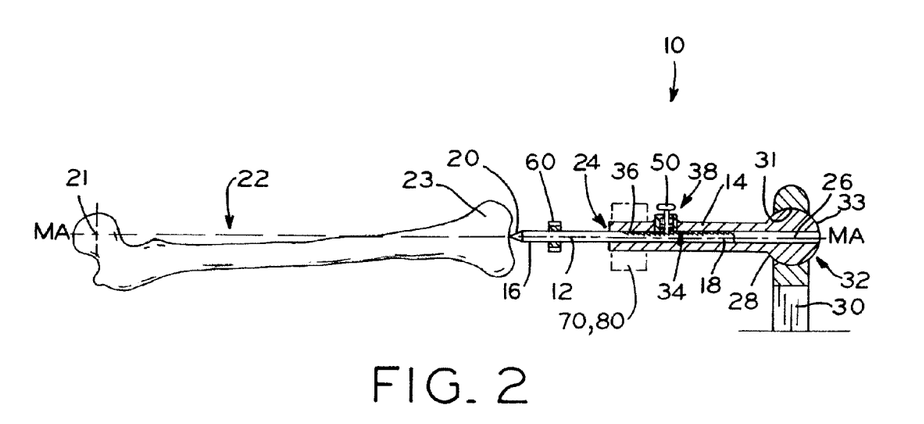
FIG. 2 is a partial cross-sectional view of the surgical instrument of FIG. 1, depicting the surgical instrument aligned with the mechanical axis of the femur.

Referring to FIGS. 1 and 2, instrument 10 is shown including rod 12 and sleeve 14. Rod 12 includes opposing first and second ends 16, 18. In one exemplary embodiment, rod 12 has a substantially circular cross-section. However, in other exemplary embodiments, rod 12 may be any elongate structure having any desired cross-section, such as a square cross-section or an oval cross-section. Although rod 12 is illustrated as being received within sleeve 14, sleeve 14 may be any form of base or body that is slideably coupled to rod 12. Further, while the longitudinal axis of sleeve 14 is substantially coincidental to the longitudinal axis of rod 12, these two axes need not be collinear. For example, rod 12 could, in certain embodiments, be coupled to a side of sleeve 14.

First end 16 of rod 12 is rotatably secured to femur 22 at stylus 20 and is positioned adjacent the intramedullary canal of femur 22 on distal end 23 of femur 22 at a centered position that lies upon mechanical axis MA (FIG. 2) and corresponds to the center of the knee joint. In the illustrated embodiment of FIGS. 1-4, stylus 20 is used to secure rod 12 to femur 22. Stylus 20 provides rod 12 with three rotational degrees of freedom, while substantially preventing translation of rod 12 relative to femur 22, i.e., stylus 20 provides rod 12 with no translational degrees of freedom. Stylus 20 includes a sharpened tip aligned with the longitudinal axis of rod 12. Using the sharpened tip, stylus 20 is passed into the distal cartilage at distal end 23 of femur 22 until stylus 20 approaches or contacts the underlying bone of femur 22 at the centered position. When in the centered position, friction between stylus 20 and the surrounding cartilage and/or bone effectively couples rod 18 to femur 22, while still allowing rod 18 to slide relative to sleeve 14 (as described in detail below).

Figure 5:
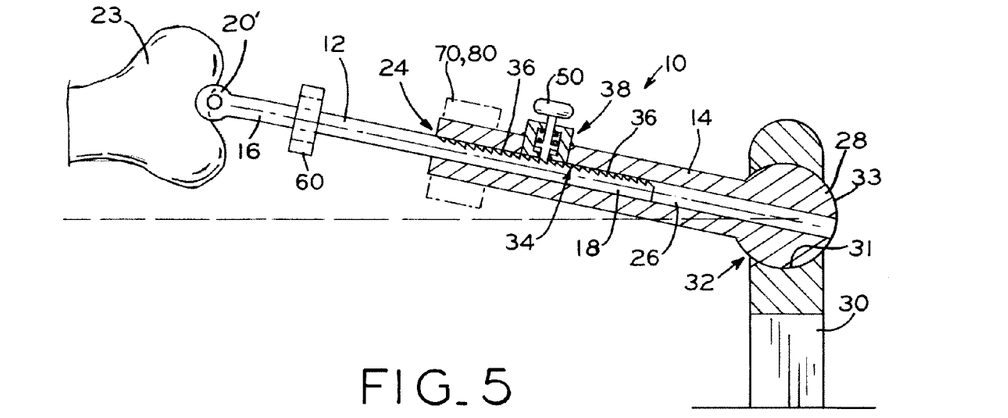
FIG. 5 is an enlarged, fragmentary view of a surgical instrument in accordance with the present disclosure depicting the surgical instrument connected to the distal end of a femur with a ball joint.
Figure 6:
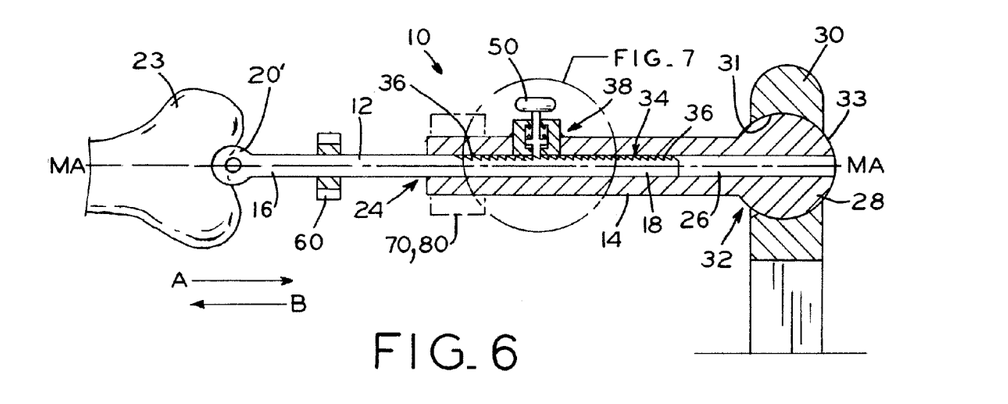
FIG. 6 is an enlarged, fragmentary view of the surgical instrument and femur of FIG. 5.

In another exemplary embodiment, shown in FIGS. 5 and 6, ball joint 21 may be used to secure rod 12 to femur 22 with three degrees of freedom, similar to stylus 20. In order to form ball joint 20', a bulbous projection formed at first end 16 of rod 12 may be received within a socket secured to femur 22. The bulbous projection at first end 16 of rod 12 may be secured within the socket in any known manner. For example, in one exemplary embodiment, the socket of ball joint 20' defines a concave inner surface that is substantially hemispherical. The socket then receives the bulbous projection at first end 16 of rod 12 therein. The socket extends around more than half of the bulbous projection of rod 12 to retain the bulbous projection of rod 12 within the socket. Additionally, the socket of ball joint 20' may be secured to femur 22 using any known fastener, such as a screw or fixation pin. Further, while ball joint 20' is described in detail herein as including a socket attached to femur 22 and a bulbous projection provided by rod 12, the components of ball joint 20' may be reversed, such that a bulbous projection is secured to femur 22 and a socket is provided at first end 16 of rod 12.

By positioning stylus 20 (or the socket of ball joint 20') on distal end 23 of femur 22 at a position that corresponds to the center of the knee joint, the tip of stylus 20 is disposed in a position that is proximate femur 22 and coincident with mechanical axis MA (FIG. 2) of femur 22, as discussed above. This connection, i.e., the connection of rod 12 to femur 22 at ball joint 20, defines a first point of rotation for instrument 10.

Second end 18 of rod 12 is positioned within sleeve 14. As shown in FIG. 1, sleeve 14 includes open end 24 and pivot end 28, with passageway 26 extending therebetween. Open end 24 provides access to passageway 26 for rod 12, which pivot end 28 provides access for a tool or marker (as described in detail below). Passageway 26 has a cross-sectional shape that is substantially similar to the cross-sectional shape of rod 12 to allow for rod 12 to slide along passageway 26. However, in order to allow for rod 12 to slide easily within passageway 26, passageway 26 may be sized to be slightly larger than rod 12. Pivot end 28 of sleeve 14 is rotatably connected to support 30 at ball joint 32. Ball joint 32 provides sleeve 14 with three rotational degrees of freedom, while substantially preventing translational movement of sleeve 14 relative to support 30, i.e., providing no translational degrees of freedom.

Referring now to FIGS. 1-4, in order to form ball joint 32, pivot end 28 of sleeve 14 includes bulbous projection 33 sized and shaped to correspond with cavity 31 formed in support 30. Cavity 31 rotatably captures bulbous projection 33, which in turn is fixed to pivot end 28 of sleeve 14 to rotatably fix sleeve 14 to base 30. In the illustrated embodiment, cavity 31 is open at the front and rear of support 30, i.e., the cavity 30 is accessible from the side of support 30 facing toward femur 22 and from the opposing side of support 30 facing away from femur 22. Thus, with passageway 26 passing through both pivot end 28 and bulbous projection 33, passageway 26 is accessible from pivot end 28. This accessibility allows a tool or marker, such as a drill bit or center punch driver, to be passed into passageway 26 to interact with rod 12 and/or femur 12, as discussed in detail below.

In an alternative method of forming ball joint 32, a bulbous projection may be formed at the end of a rod extending outwardly from support 30 in a direction transverse to the longitudinal axis of support 30. The bulbous projection may be received within a socket formed at pivot end 28 of sleeve 14 and may be secured within the socket in any known manner. For example, in one exemplary embodiment, the socket of sleeve 14 defines a concave inner surface that is substantially hemispherical. The socket then receives the bulbous projection of support 30 therein. In one exemplary embodiment, the socket of sleeve 14 extends around more than half of the bulbous projection of support 30 to retain the bulbous projection within the socket.

The rotatable connection of sleeve 14 to support 30 at ball joint 32 defines a second point of rotation for instrument 10. While the connections between both rod 12 and femur 22 and sleeve 14 and support 30 are described and depicted herein as stylus 20 and/or ball joints 20', 32, any type of connection may be used that provides rod 12 and sleeve 14 with three rotational degrees of freedom, while substantially preventing translation of both rod 12 relative to femur 22 and sleeve 14 relative to support 30.

Figure 7:
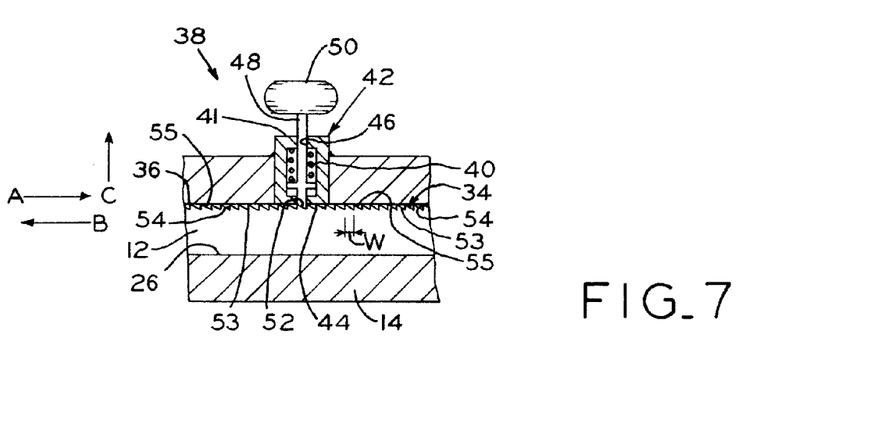
FIG. 7 is a fragmentary, cross-sectional view of a portion of a ratchet mechanism used in conjunction with the surgical instrument of FIG. 4.

In one exemplary embodiment, shown in FIGS. 1-8, rod 12 and sleeve 14 cooperate to define a retention mechanism, such as a ratchet mechanism (FIG. 7), which provides coarse measurement capabilities and locks rod 12 with respect to sleeve 14. In addition, rod 12 and sleeve 14 may each be operatively coupled with a high-resolution measurement device or indicator, such as a linear variable differential transformer (LVDT) (FIG. 8) or a dial indicator (FIG. 9). The high-resolution indicator provides fine measurement capability, thereby facilitating precise determination of the orientation of instrument 10 in which the longitudinal axis of rod 12 and mechanical axis MA of femur 22 are aligned (as discussed in more detail below).

Where instrument 10 includes a ratchet mechanism, second end 18 of rod 12 includes rack 34 having teeth 36. Rack 34 cooperates with pawl 38 of sleeve 14 to allow for translation of rod 12 into sleeve 14, while preventing translation of rod 12 out of sleeve 14 via open end 24. Specifically, referring to FIG. 7, pawl 38 is downwardly biased by spring 40, which is captured between end 41 of pawl housing 42 and outwardly extending shoulder 44 of pawl 38. End 41 of pawl housing 42 includes opening 46 through which shaft 48 of pawl 38 extends. Knob 50 is positioned on a first end of shaft 48 and teeth engagement surface 52 is defined at the opposing, second end of shaft 48. As shown in FIG. 7, engagement surface 52 of pawl 38 is angled to allow engagement surface 52 to contact and lie along upper surface 55 of one of teeth 36. Additionally, the shape the second end of shaft 48 also corresponds to and fits within grooves 53 defined between adjacent teeth 36.

Figure 4:
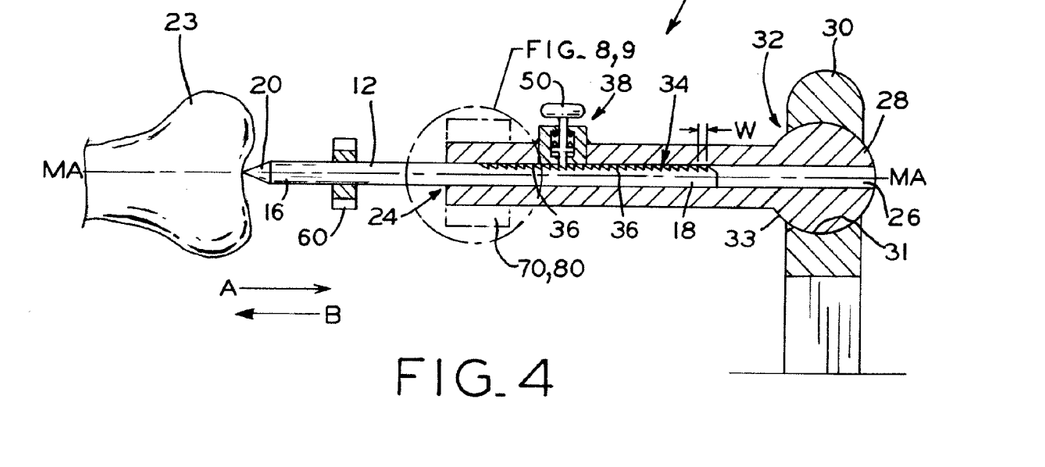
FIG. 4 is an enlarged, fragmentary view of the surgical instrument and femur of FIG. 2.

As indicated above, rack 34 and pawl 38 cooperate to define a ratchet mechanism that allows for translation of rod 12 relative to sleeve 14 in a first direction, i.e., the direction of arrow A of FIG. 4, while preventing translation of rod 12 relative to sleeve 14 in a second, opposite direction, i.e., the direction of arrow B of FIG. 4. Specifically, referring to FIG. 7, as rod 12 is advanced in the direction of arrow A, engagement surface 52 of pawl 38 slides along upper surface 55 of one of teeth 36, causing pawl 38 to be advanced upwardly in the direction of arrow C of FIG. 7 and to compress spring 40. As rod 12 continues to move in the direction of arrow A, engagement surface 52 eventually passes over upper surface 55 of one of teeth 36. At this point, spring 40 biases pawl 38 downwardly into groove 53 defined between two adjacent teeth 36, such that engagement surface 52 contacts upper surface 55 of another of teeth 36.

Once in this position, rack 34 and pawl 38 cooperate to prevent movement of rod 12 in the direction of arrow B. Specifically, in the position shown in FIG. 7, pawl 38 contacts the substantially flat back surface 54 of one of teeth 36. Due to this interaction and the biasing force of spring 40, rod 12 is prevented from moving in the direction of arrow B. In order to remove rod 12 from sleeve 14, an individual may grasp knob 50 and apply a force to knob 50 in the direction of arrow C that is sufficient to overcome the biasing force of spring 40. With a force sufficient to overcome the biasing force of spring 40 applied to knob 50, spring 40 is compressed between end 41 of pawl housing 42 and shoulder 44 of pawl 38 to allow rack 34 of rod 12 to pass beneath engagement surface 52 of shaft 48.

The cooperation between rack 34 and pawl 38 allow a coarse adjustment of rod 12 with respect to sleeve 14. For example, when a movement of rod 12 is sufficient to advance engagement surface 52 of shaft 48 from one flat back surface 54 to the next neighboring flat back surface 54 along rack 34, rod 12 has advanced along arrow A by width W (FIGS. 4 and 7) of one of teeth 36. This measurement may be said to have a "coarse" resolution, in that any increment of adjustment smaller than width W yields no new measurement information.

Figure 8:
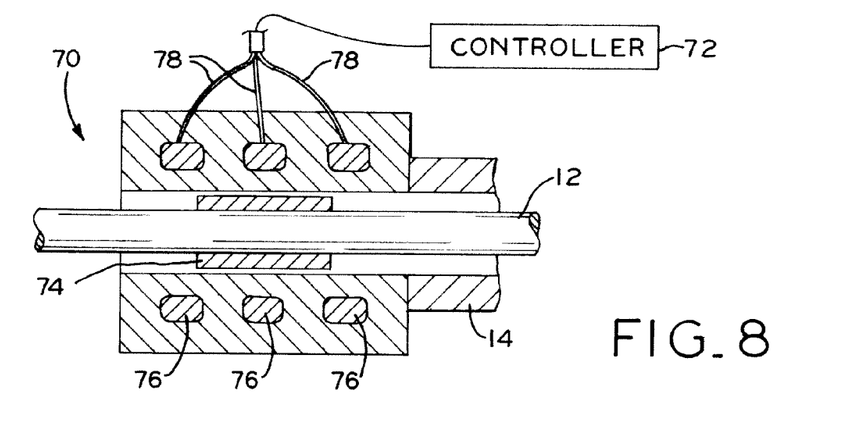
FIG. 8 is a fragmentary, cross-sectional view of a portion of a linear variable differential transformer used in conjunction with the surgical instrument of FIG. 4
Figure 9:
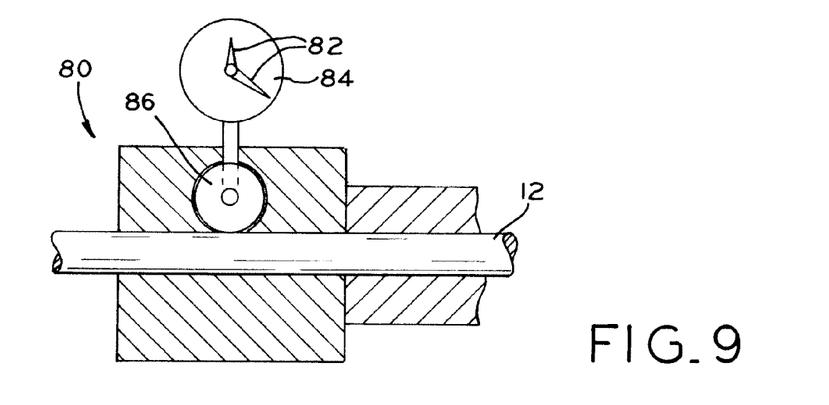
FIG. 9 is a fragmentary, cross-sectional view of a portion of a dial indicator used in conjunction with the surgical instrument of FIG. 4.

Referring now to FIG. 8, LVDT 70 may be used to provide a finer measurement resolution. LVDT measures linear displacement of rod 12 using solenoidal coils 76 placed end-to-end around a tube with an alternating current driven therethrough in a conventional manner. LVDT 70 is mounted to sleeve 14 and ferromagnetic core 74 is coupled to rod 12. Movement of cylindrical ferromagnetic core 74 attached to rod 12 changes voltages induced in one or more of the solenoidal coils. This changing voltage may be used to measure the relative position of ferromagnetic core 74 relative to LVDT 70. LVDT 70 may have a sensitivity that allows measurements of motions smaller than width W, so LVDT may be used to measure movements of rod 12 along a single one of teeth 36. The voltage output by LVDT 70 may be output via wires 78 to controller 72, which may convert the voltage to position and/or measurement information and display the information in a conventional manner. Although ferromagnetic core 74 is illustrated as being mounted upon rod 12, core 74 may also be contained within or otherwise made integral to rod 12.

Similarly, referring now to FIG. 9, dial indicator 80 may be used in addition to or in place of LVDT 70 for high-resolution measurement of the position and movement of rod 12. Dial indicator 80 is a conventional measurement device, but is adapted to measure movement of rod 12. Dial indicator 80 is mounted to sleeve 14 and operatively coupled to rod 12, such as by roller 86, so that movement of rod 12 relative to sleeve 14 moves measurement needles 82 on display 84 of dial indicator 80. When an inflection point has been reached, indicating an alignment of the longitudinal axis of rod 12 with mechanical axis MA as described below, one of measurement needles 82 will change direction, thereby allowing an intuitive and easily recognizable indication of the inflection point.

Base 30 has sufficient rigidity to resist excessive deflection or bending under the forces experienced by instrument 10 in the course of use. For example, where instrument 10 includes LVDT 70, dial indicator 80, or another high-resolution measurement device or indicator with sensitive measurement capability, deflection in base 30 is small enough to have a negligible effect on measurement accuracy and precision. In an exemplary embodiment, base 30 may comprise a series of tubes or bars interconnected into a truss structure. Base 30 may also be shaped to facilitate use with a patient lying on a surface such as an operating table. In an exemplary embodiment (not shown), base 30 includes a base with tubes extending upwardly therefrom such that instrument 10 is elevated above the patient support surface, thereby facilitating operation on a bent knee.

In order to utilize instrument 10 to determine the location of mechanical axis MA (FIG. 2) of femur 22, support 30 may be secured in an arbitrary position that is located distally of distal end 23 of femur 22. For example, support 30 may be secured to an operating table upon which a patient is positioned or may be secured directly to the floor of an operating room. The torso of the patient is then secured to the operating table to prevent movement of the patient's upper body relative to support 30. With sleeve 14 secured to support 30 at ball joint 32, rod 12 is positioned within passageway 26 of sleeve 14 and advanced so that the first of teeth 36 of rack 34 engage pawl 38 to secure rod 12 in position within sleeve 14.

First end 16 of rod 12 is secured to distal end 23 of femur 22 using stylus 20 or ball joint 20', which is positioned adjacent to an opening to the intramedullary canal of the femur at a point that corresponds to the center of the knee joint and, thus, is coincident with mechanical axis MA. In one exemplary embodiment, stylus 20 is passed through the cartilage in the vicinity of distal end 23 of femur 20, as discussed above. In another exemplary embodiment, a socket of ball joint 20' is secured to femur 22, also described in detail above, using a bone screw. In either embodiment, first end 16 of rod 12 is rotatably secured to distal end 23 of femur 22. In order to align stylus 20 or the socket of ball joint 20' with first end 16 of rod 12, sleeve 14 and/or femur 22 and, correspondingly, a patient's leg, may be manipulated. Additionally, it may be necessary to pull upward on knob 50 in the direction of arrow C of FIG. 7 to overcome the biasing force of spring 40 in order to release pawl 38. This allows for rod 12 to be translated in the direction of arrow B of FIG. 4 and may facilitate alignment of first end 16 of rod 12 with the socket of ball joint 20. First end 16 is then secured to the socket of ball joint 20 to position instrument 10 substantially as shown in FIGS. 1 and 3.

Figure 3:
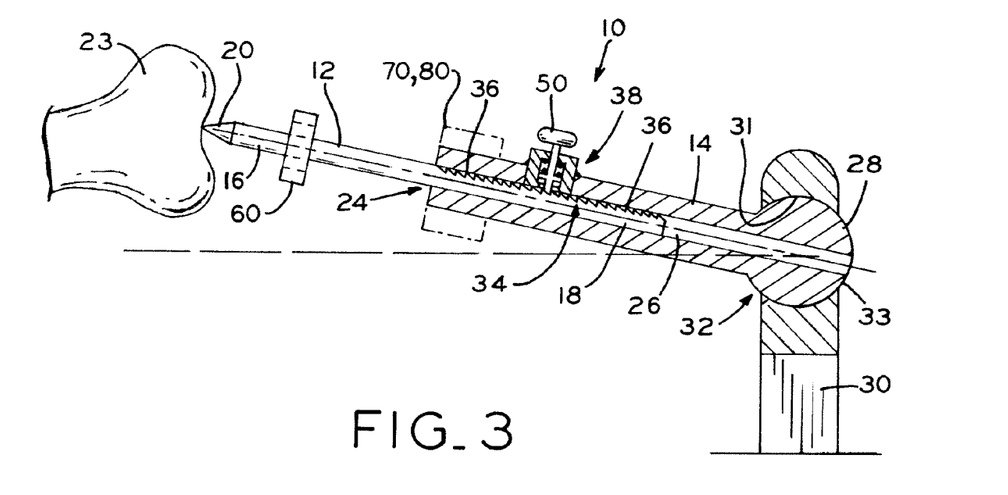
FIG. 3 is an enlarged, fragmentary view of the surgical instrument and femur of FIG. 1.

With femur 22 and instrument 10 in the position shown in FIGS. 1, 3 and 5, femoral head 21 (FIG. 1) of femur 22 is rotated against the acetabulum of the hip joint. As femur 22 rotates, rod 12 may be advanced into sleeve 14 in the direction of arrow A. As indicated above, the ratchet mechanism created by rack 34 and pawl 38 prevents movement of femur 22 in the direction of arrow B of FIG. 4 as femur 22 is rotated. With sufficient rotation of femur 22, rod 12 will be advanced far enough into sleeve 14, that any further advancement of rod 12 into sleeve 14 achieved by rotation of femur 22 is insufficient to engage the next one of teeth 36 on rack 34. Once in this position, as shown in FIGS. 2 and 4, an estimation of minimum distance between the first and second points of rotation, i.e., between the connection of rod 12 and femur 22 at ball joint 20 and the connection of sleeve 14 and support 30 at ball joint 32, is established. As noted above, this is a relatively coarse measurement, in that femur 22 will typically remain rotatable through a relatively small range of motion.

A more accurate minimum distance between the first and second points of rotation may then be found by further rotating femur 22 so that LVDT 70 and/or dial indicator 80 registers further motion of rod 12 with respect to sleeve 14. Rotation of femur 22 will either increase or decrease the distance between the first and second points of rotation, and rotation of femur 22 through the minimum distance will cause an inflection in the distance measurement from decreasing to increasing. As noted above, this inflection would be visually indicated on dial indicator 80 by needle 82 changing direction. The desired inflection may also be audibly or visually indicated by controller 72, for example, when a minimum distance is recorded by LVDT 70. A series of such inflections around the relatively small range of motion of femur 22 (due to the interaction of rack 34 and pawl 38, as discussed above) will yield an inflection with a minimum distance lower than other inflections. More inflections will result in ever-more-perfect minimum distance calculations.

Once a minimum distance is established between the first and second points of rotation, the longitudinal axis of rod 12 is aligned such that it is collinear with mechanical axis MA of femur 22. By extending the longitudinal axis of rod 12 to femoral head 21 (FIG. 2) of femur 22, mechanical axis MA of femur 22 is identified.

Once in this position, an additional surgical instrument, such as surgical instrument 60, may be advanced along rod 12 to position surgical instrument 60 adjacent distal end 23 of femur 22 in alignment with mechanical axis MA of femur 22. In one exemplary embodiment, surgical instrument 60 is a cut guide. Once in this position, additional surgical procedures, such as the resection of distal end 23 of femur 22, may be performed using surgical instrument 60. In one exemplary embodiment, surgical instrument 10 is removed from femur 22 prior to performing any additional surgical procedures. In another exemplary embodiment, surgical instrument 10 remains in position and provides a constant identification of mechanical axis MA of femur 22 during the additional procedures performed by the surgeon.

Figure 10:
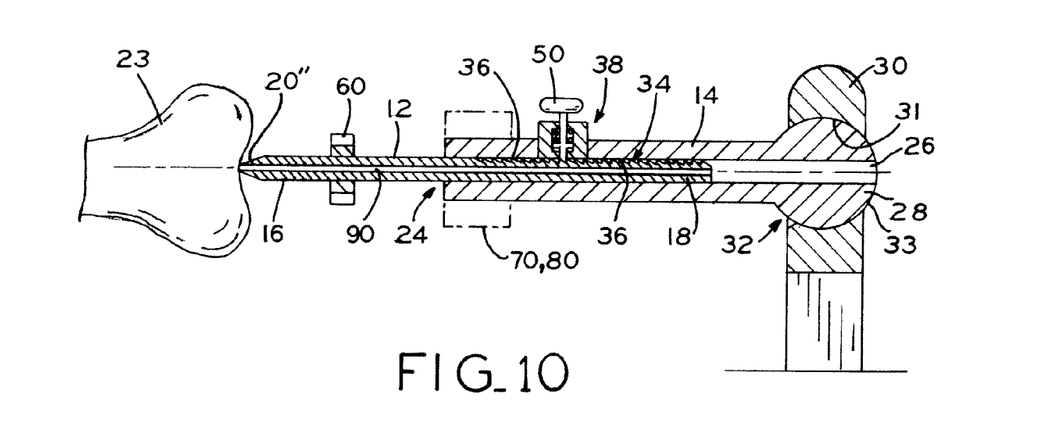
FIG. 10 is an enlarged, fragmentary view of the surgical instrument of FIG. 2, shown with a hollow rod.

Further, once mechanical axis MA of femur 22 is established as described in detail above, mechanical axis MA of femur 22 may be marked for later reference and/or attachment of surgical instruments, such as by fixing pins to femur 22 or scoring femur 22. As illustrated in FIGS. 1-6, for example, a tool (not shown) may be passed through passageway 26 via pivot end 28 and impacted against the rear portion of rod 12, thereby driving stylus into femur 22 in a similar manner as a center punch of harder material is used to mark a softer material. Alternatively, as shown in FIG. 10, rod 12 may include bore 90 therethrough. A tool, such a drill bit, may be passed through passageway 26 and then through bore 90, ultimately contacting femur 22 to mark or drill femur 22 at or along mechanical axis MA. In this embodiment, stylus 20" is distinguished from stylus 20 in that stylus 20" has a somewhat more blunt tip owing to bore 90. However, stylus 20" may still be sufficiently sharp to penetrate the cartilage proximate distal end 23 of femur 20, as described above with respect to stylus 20.

In other exemplary embodiments, surgical instrument 10 may lack a retention mechanism for securing rod 12 in position within passageway 26. Thus, in these embodiments, rack 34 may be absent from rod 12 and rod 12 may include a scale, gradations or another indicator that provides an indication or coarse measurement of the distance that rod 12 has been advanced into passageway 26 of sleeve 14. In these embodiments, the surgeon may visually track the translation of rod 12 relative to sleeve 14 to determine the resulting position of femur 22 and rod 12 when the minimum distance between the first and second points of rotation is achieved. By repositioning rod 12 to achieve the minimum distance, the location of mechanical axis MA of femur 22 can be identified. In a further embodiment, surgical instrument 10 may include LVDT 70, dial indicator 80, and/or another measurement device or indicator, and may not include a ratchet mechanism such as rack 34 and pawl 38. In this embodiment, mechanical axis MA is identified by finding the minimum distance between the first and second points of rotation, as discussed herein, with rod 12 freely moveable within sleeve 14.

For example, in another exemplary embodiment (not shown), an alternative indicator may include two rotational encoders and one linear encoder positioned on surgical instrument 10 to monitor the movement of the end point of surgical instrument 10 in three dimensional space. Additionally, with this configuration, the user may move femur 22 around arbitrarily in space, without necessarily ever passing through the minimum distance point, and then the collected three dimensional data can be used to compute the center of a sphere, which would be location of the center of femoral head 21, and then the minimum distance point could be computed from the location of the center of femoral head 21 within the coordinate space of surgical instrument 10, assuming that the origin of the coordinate space is coincident with the encoder centers, as the point on the femoral head center vector that is closer to the origin by the computed sphere radius. The user could then be guided, such as by the use of a digital display, to position the device at the minimum distance point directly, allowing the user to achieve the same result, i.e., position femur 22 in an aligned position with respect to mechanical axis MA of femur 22.

Additionally, in this embodiment, the user is effectively computing the length of femur 22, which is a known current unmet need for hip replacement procedures. In making this calculation, the device would be attached to the knee in a non-invasive manner, since the knee would not be the operative joint for a hip procedure. Such non-invasive attachment could be accomplished by any known methods.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical instrument for determining the mechanical axis of a bone, the instrument comprising:
   a support;
   an elongate base having a pivot end rotatably coupled to said support with three degrees of rotational freedom;
   an elongate rod having a bone-contacting end adapted to be rotatably coupled to a bone with three rotational degrees of freedom, said rod slidably coupled to said base; and
   an indicator in communication with said base and said rod, said indicator measuring a relative position of said rod to said base, wherein the elongate rod and the elongate base are configured such that as the bone is rotated, the elongate rod slides relative to the base, and when the relative position between the rod and the base is at a minimum distance, the elongate rod is substantially collinear with the mechanical axis of the bone.

2. The surgical instrument of claim 1, further comprising a ratchet mechanism including a rack disposed on the rod and a pawl coupled to said base, said pawl biased toward said rack, said ratchet mechanism operable to allow a reduction in a distance between said bone-contacting end of said rod and a point on said base, said ratchet mechanism operable to prevent a lengthening of said distance between said bone-contacting end of said rod and said point on said base.

3. The surgical instrument of claim 1, wherein said elongate base comprises a sleeve with a passageway extending through the entirety of said sleeve along a longitudinal axis of said base, said rod received within said passageway and accessible via said passageway.

4. The surgical instrument of claim 3, wherein said bone-contacting end of said elongate rod comprises a stylus having a sharpened end, said surgical instrument further comprising an impact tool receivable within said passageway of said sleeve, said impact tool cooperating with said rod to transfer an impact from said impact tool to said stylus, whereby said stylus marks the mechanical axis of the bone when the impact is received.

5. The surgical instrument of claim 3, wherein said rod includes a bore along a longitudinal axis of said rod, said bore extending entirely through a longitudinal extent of said rod, said surgical instrument further comprising a marking tool receivable within said bore of said rod, said marking tool operable to mark the mechanical axis of the bone when said marking tool is received within said bore of said rod.

6. The surgical instrument of claim 1, wherein said bone-contacting end of said elongate rod comprises a stylus, said stylus including a sharpened end operable to pierce cartilage proximate an end of the bone to couple said stylus to the end of the bone, whereby said rod is prevented from translating relative to the bone when said stylus is coupled to the bone.

7. The surgical instrument of claim 1, wherein said bone-contacting end of said elongate rod comprises a ball joint, said ball joint including an aperture operable to couple to an end of the bone, whereby said rod is prevented from translating relative to the bone when said ball joint is coupled to the bone.

8. The surgical instrument of claim 1, wherein said elongate base comprises a ball at said pivot end, said support comprises a socket sized and shaped to receive said ball of said base, whereby said ball of said elongate base cooperates with said socket of said support to define a ball joint.

9. A surgical instrument for determining the mechanical axis of the bone, the instrument comprising:
 a support for supporting the surgical instrument;
 an elongate base having a pivot end rotatably coupled with said support, said elongate base having three degrees of rotational freedom relative to the bone, said elongate base constrained from translation relative to the femur;
 an elongate rod having a bone-contacting end adapted to be rotatably coupled to a bone with three rotational degrees of freedom relative to the bone, said rod constrained from translation relative to the femur, said rod slidably coupled to said base; and
 a measurement device operatively coupled to said rod and said body, said measurement device for measuring a distance between said bone-contacting end of said rod and a point on said base, wherein the elongate rod and the elongate base are configured such that as the femur is rotated, the elongate rod slides relative to the base, and when the distance between said bone-contacting end of said rod and the point on said base is at a minimum, the elongate rod is substantially collinear with the mechanical axis of the bone.

10. The method of claim 9, wherein said measurement device comprises at least one of a linear variable differential transformer, a dial indicator, a scale disposed on said elongate rod, and a ratchet mechanism.

11. The method of claim 9, further comprising a mechanism for preventing a lengthening of said distance between said bone-contacting end of said elongate rod and said point on said elongate base, said mechanism for preventing a lengthening of said distance operable to allow a reduction of said distance.

12. The method of claim 11, wherein said mechanism for preventing a lengthening of said distance comprises a ratchet mechanism including a rack disposed on said rod and a pawl coupled to said base, said pawl biased toward said rack.

* * * * *